(12) United States Patent
Maston

(10) Patent No.: US 9,968,420 B1
(45) Date of Patent: May 15, 2018

(54) TOOTH PROTECTION DEVICE

(71) Applicant: Beverly Maston, Medford, OR (US)

(72) Inventor: Beverly Maston, Medford, OR (US)

(*) Notice: Subject to any disclaimer, the term of this patent is extended or adjusted under 35 U.S.C. 154(b) by 270 days.

(21) Appl. No.: 14/959,674

(22) Filed: Dec. 4, 2015

(51) Int. Cl.
*A61C 5/14* (2006.01)
*A61M 31/00* (2006.01)

(52) U.S. Cl.
CPC ............ *A61C 5/14* (2013.01); *A61M 31/00* (2013.01); *A61M 2210/0637* (2013.01)

(58) Field of Classification Search
CPC ............ A61M 31/00; A61M 31/002; A61M 2210/0637; A61M 2210/0631; A61M 2210/0625; A63B 71/085; A63B 71/081; A61C 19/063; A61C 19/06; A61C 5/90; A61C 7/08; A61C 19/066
See application file for complete search history.

(56) References Cited

U.S. PATENT DOCUMENTS 4,093,708 A * 6/1978 Zaffaroni .................. A61F 6/14
424/427

* cited by examiner

*Primary Examiner* — Victoria J Hicks
(74) *Attorney, Agent, or Firm* — Gulf Coast Intellectual Property Group

(57) ABSTRACT

A tooth protection device that is operable to provide impact protection and thermal protection for a damaged tooth within a user's mouth. The tooth protection device includes a base layer that is rectangular in shape and is manufactured from a malleable gum resin. The base layer further has an internal thermal layer that is operable to provide a thermal barrier so as to inhibit the change of temperature proximate the tooth. The base layer further includes a medicament impregnated therein that is operable to provide pain relief to the area. The medicament comprises a natural medicament or a synthetic medicament. The base layer extends from the gum line on a first side of a tooth, across the top of the tooth and reaching the gum line on the second side of the tooth.

11 Claims, 2 Drawing Sheets

TOOTH PROTECTION DEVICE

PRIORITY UNDER 35 U.S.C. SECTION 119(E) & 37 C.F.R. SECTION 1.78

This nonprovisional application claims priority based upon the following prior United States Provisional Patent Application entitled: Tooth Protector, Application No. 62/088,869 filed Dec. 8, 2014, in the name of Beverly Maston, which is hereby incorporated by reference for all purposes.

FIELD OF THE INVENTION

The present invention relates generally to dental care, more specifically but not by way of limitation a tooth protection device that is configured to be superposed at least one tooth and provide a thermal and impact barrier for temporary protection of a damaged tooth.

BACKGROUND

Dental emergencies are quite common and are created from a variety of causes. From chipping a tooth in an accident to having a dental filling or crown dislodge, these events can be very painful and be quite inconvenient. Many times a person suffering from a dental emergency will not be able to seek immediate medical care. Facilities such as emergency rooms are not equipped with dental staff to provide emergency care afterhours. Dentist offices are typically not open on the weekend or in the evening and the lack of availability can lead to a sufferer having to wait for a couple of days. This creates quite a dilemma for the sufferer as the pain can typically not be completely managed with conventional over the counter remedies.

One problem with pain management for dental emergencies is the limited options that a patient has to manage the pain while awaiting treatment from a dentist. One option is a topical analgesic that is applied directly to the affected tooth. While this can be temporarily effective, these remedies can often wash away and only last a few hours. Oral analgesics can also be utilized but are typically ineffective at managing the severity of the pain associated with many dental emergencies. None of the aforementioned address the affect that temperature change has on the damaged tooth. Temperature changes in the mouth from either drinking a liquid or just opening the mouth has a significant impact on the intensity of the pain and can increase the pain felt by the patient quite dramatically.

Accordingly, there is a need for a tooth protection device that can provide temporary relief from dental pain wherein the tooth protection device can be superposed the affected area so as to provide impact protection and a thermal barrier.

SUMMARY OF THE INVENTION

It is the object of the present invention to provide a tooth protection device that is operable to provide temporary relief of tooth pain that is configured to be superposed a tooth or a plurality of teeth is planar and flexible.

Another object of the present invention is to provide a tooth protection device that includes covering layer that includes a gum resin layer and a thermal layer internally present within the gum resin layer.

A further object of the present invention is to provide a tooth protection device that is operable to provide impact and thermal protection of a damage tooth that is configured to be superposed a damaged area and wherein the gum layer has sufficient adhesive qualities so as to maintain the position of the tooth protection device.

Still another object of the present invention is to provide a tooth protection device operable to provide thermal and impact protection to a damaged tooth wherein the gum resin layer further includes a medicament such as a topical analgesic.

An additional object of the present invention is to provide a tooth protection device operable to provide relief from tooth pain wherein the covering layer may further include an adhesive to assist in the maintenance of the placement thereof.

Yet a further object of the present invention is to provide a tooth protection device operable to provide relief from tooth pain wherein the internal thermal layer is manufactured from a metalized poly film.

Another object of the present invention is to provide a tooth protection device that is operable to provide both thermal protection and impact protection for a damaged tooth wherein the medicament can be a natural remedy or a synthetic compound.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
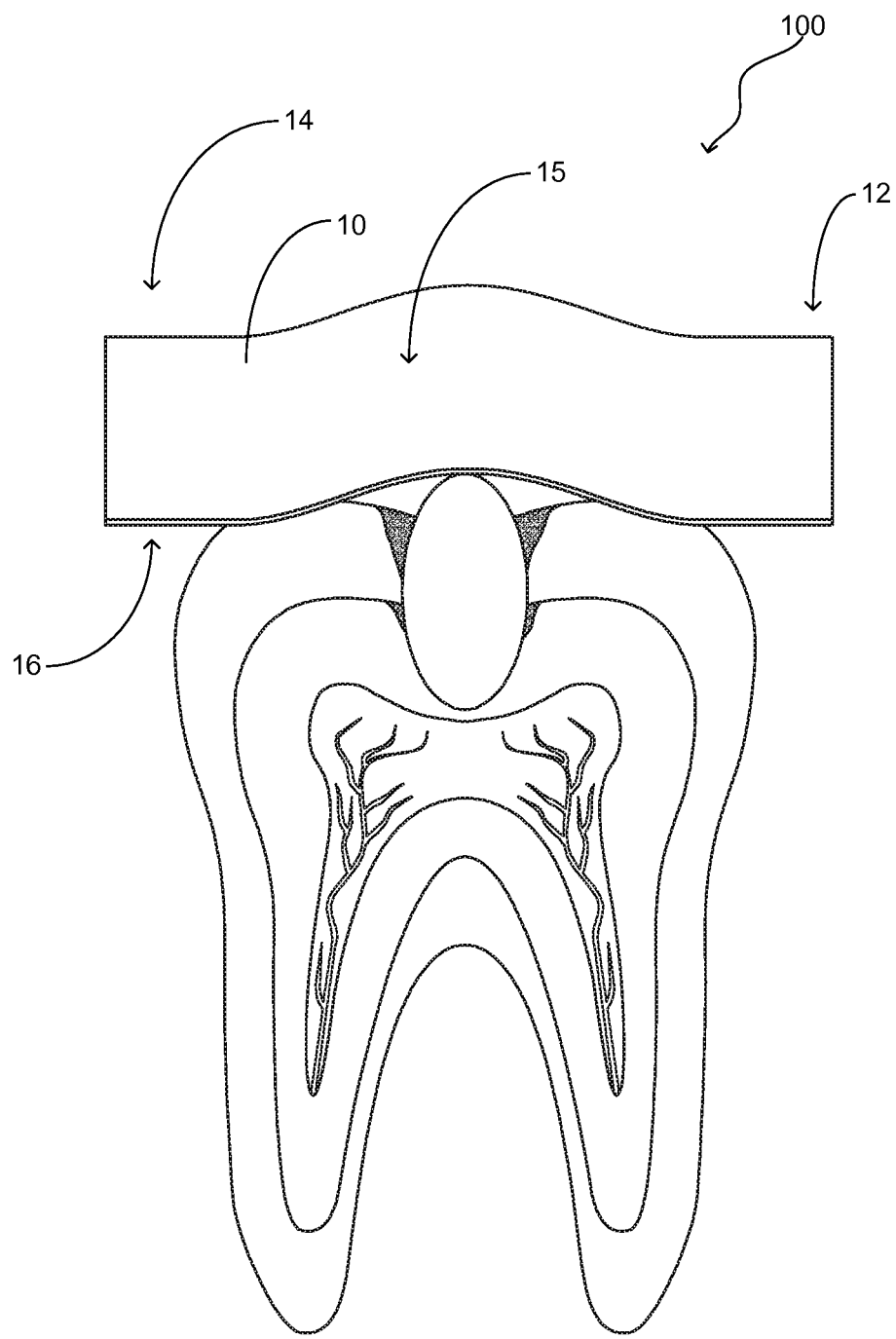
FIG. 1 is a side view of the present invention superposed an exemplary damaged tooth.

Referring now to the drawings submitted herewith, wherein various elements depicted therein are not necessarily drawn to scale and wherein through the views and figures like elements are referenced with identical reference numerals, there is illustrated a tooth protection device 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Figure 2:
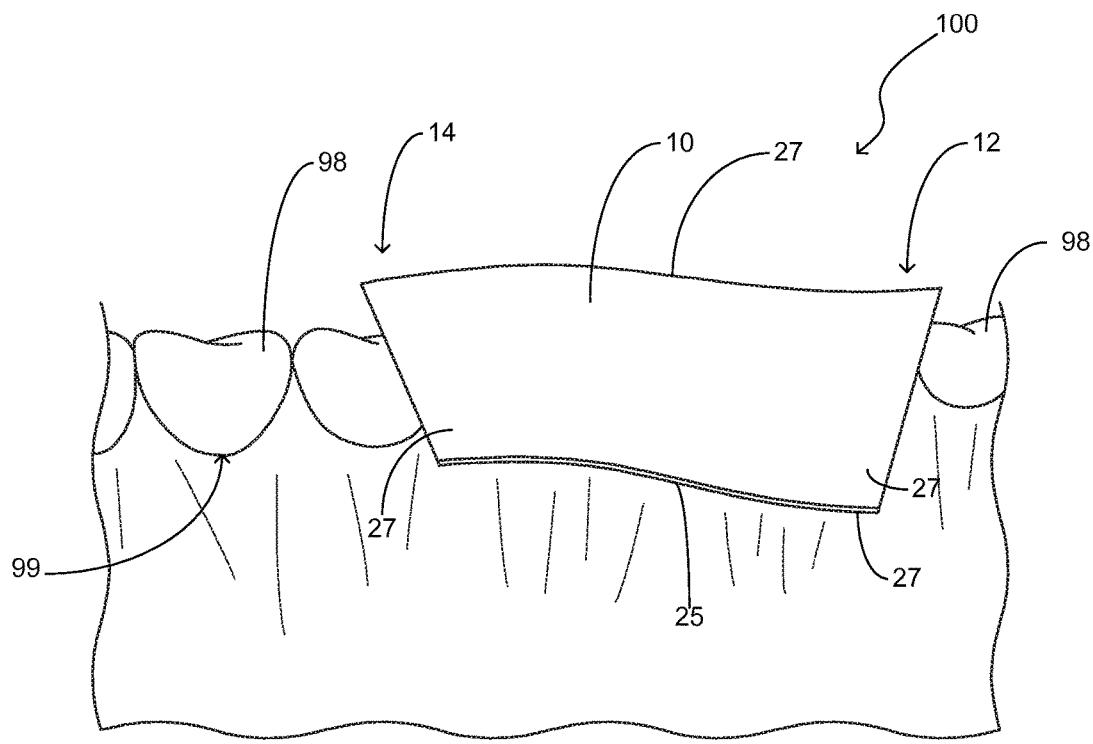
FIG. 2 is a perspective view of the present invention superposed a plurality of exemplary teeth.

Referring now to the Figures herein, the tooth protection device 100 includes a base layer 10 that is generally rectangular in shape having a first end 12 and a second end 14. The base layer 10 includes an upper surface 15 and a lower surface 16 and the base layer 10 is manufactured from a malleable material such as but not limited to resin. While no particular resin is required, it is desired within the scope of the present invention that the base layer 10 is manufactured from a food grade natural resin such as but not limited to natural mastic resin as the tooth protection device 100 is utilized orally by a user. The base layer 10 is manufactured to a suitable size so as to be superposed at least two teeth 98 wherein both sides of the teeth 98 are cover in addition to the top of the teeth 98. The tooth protection device 100 provides temporary relief of pain by assisting in the control of temperature changes proximate the teeth covered by the base layer 10. Utilizing a base layer 10 that is malleable and sized to cover the teeth as described herein provides an effective technique of insulating the teeth from changes in temperature due to the consumption of a liquid or the opening of the mouth. By way of example but not limitation, as shown herein in FIG. 2, the lateral edge 25 extends to the gum line 99 and while not particularly illustrated herein the opposing side of the teeth 98 is covered in a similar manner. While no particular thickness of the base layer is required, good results have been achieved utilizing a base layer 10 that is approximately two to four millimeters in thickness. The structural material of the base layer 10, gun resin further promotes adherence to the teeth 98 so as to ensure a seal and provide the protection as described herein. The base layer 10 further provides impact protection due to the properties of the gum resin. While not particularly illustrated in the Figures herein, it is further contemplated that the base layer 10 could include an adhesive layer disposed on the lower surface 16 thereof proximate the perimeter 27 so as to provide an alternate or added technique to ensure the securing of the tooth protection device 100. Those skilled in the art will recognize that numerous types of adhesives could be utilized on the base layer 10 in order to achieve the desired aforementioned functionality.

Figure 3:
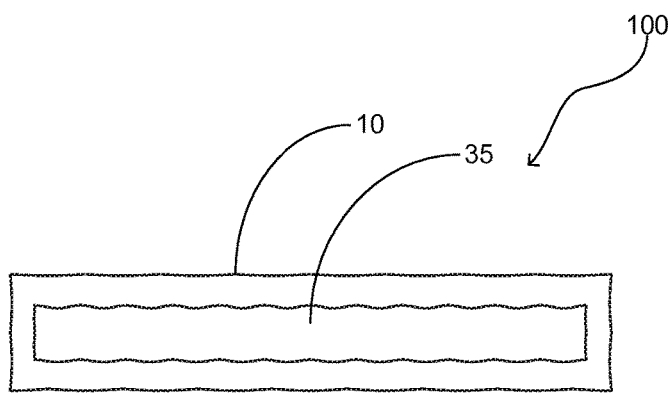
FIG. 3 is a cross-sectional diagram of the present invention.

Shown in particular in FIG. 3, the base layer 10 includes an internal thermal layer 35. The internal thermal layer 35 is operable to thermally isolate the teeth 98 on which the tooth protection device 100 has been superposed and functions to maintain the temperature thereof. The internal thermal layer 35 is sized so as to be at least ninety percent of the area as the base layer 10 and is manufactured from a suitable flexible thermal material such as but not limited to metalized poly film. Those skilled in the art will recognize that numerous different types of materials could be utilized for the internal thermal layer 35.

The base layer 10 is impregnated with a medicament (not illustrated herein) so as to provide pain relief to the area that the tooth protection device 100 has been superposed. The medicament is impregnated into the base layer 10 utilizing suitable durable techniques and it is contemplated within the scope of the present invention to be provided both in a natural form and a synthetic form. By way of example but not limitation, a natural form of medicament impregnated into the base layer 10 could be peppermint or *Echinacea*. While no particular concentration of the aforementioned natural medicament is required, good results have been achieved utilizing a natural medicament with a range of 1:5 to 1:25 concentration by weight. For a synthetic embodiment of the present invention, it is contemplated within the scope of the present invention to utilize a topical analgesic such as but not limited to lidocaine, wherein the lidocaine is impregnated into the base layer 10 utilizing suitable durable techniques. While no specific concentration of lidocaine is required, good results have been achieve utilizing a 0.5 to 5% concentration. It is further contemplated within the scope of the present invention that the base layer 10 be treated with a suitable anti-bacterial compound in order to prevent infection of the teeth 98 with which the tooth protection device 100 has been engaged.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A tooth protection device operable to provide protection to a damaged tooth comprising:
   a base layer, said base layer having an upper surface and a lower surface, said base layer having a first end and a second end, said base layer being manufactured from a malleable material, said base layer configured to be superposed onto at least one tooth, said base layer further including a medicament, wherein the medicament is operable to provide pain relief to an area onto which the tooth protection device is superposed, said base layer being manufactured from a gum resin, said base layer having opposing lateral edges, said base layer configured to extend intermediate opposing gum lines of the at least one tooth, said base layer being two to four millimeters in thickness;
   a thermal layer, said thermal layer being disposed within said base layer, said thermal layer being configured to assist in avoidance of temperature change of the at least one tooth onto which the base layer is superposed, said thermal layer being a metalized poly film.

2. A tooth protection device operable to provide pain relief to a damaged tooth and further insulate the damaged tooth from temperature change comprising:
   a base layer, said base layer being rectangular in shape and planar in manner, said base layer having an upper surface and a lower surface, said base layer having a first end and a second end, said base layer being manufactured from a malleable gum resin material, said base layer configured to be superposed onto at least one tooth;
   a thermal layer, said thermal layer being disposed within said base layer, said thermal layer being a metalized poly film;
   a medicament, said medicament being impregnated into said base layer, said medicament operable to provide pain relief to the at least one tooth onto which the tooth protection device is superposed.

3. The tooth protection device as recited in claim 2, wherein the thermal layer extends intermediate said first end and said second end of said base layer.

4. The tooth protection device as recited in claim 3, wherein the base layer is a natural gum resin.

5. The tooth protection device as recited in claim 4, wherein the base layer is two to four millimeters in thickness.

6. The tooth protection device as recited in claim 5, wherein the medicament is selected from one of two groups: natural or synthetic.

7. A tooth protection device that is operable to provide impact and thermal protection to a damaged tooth comprising:
   a base layer, said base layer being rectangular in shape and planar in manner, said base layer having an upper surface and a lower surface, said base layer having a first end and a second end, said base layer having opposing lateral edges, said base layer being manufactured from a malleable gum resin material, said base layer configured to be superposed onto at least one tooth;
   a thermal layer, said thermal layer being disposed within said base layer, said thermal layer being a metalized poly film;
   a medicament, said medicament being impregnated into said base layer, said medicament operable to provide pain relief to the at least one tooth onto which the tooth protection device is superposed; and
   wherein the base layer is configured to extend intermediate opposing gum lines of the tooth.

8. The tooth protection device as recited in claim 7, wherein the medicament is selected from one of the following groups: a natural medicament or a synthetic medicament.

9. The tooth protection device as recited in claim 8, wherein the base layer further includes an adhesive, said adhesive being present on the lower surface thereof.

10. The tooth protection device as recited in claim 9, wherein the base layer is two to four inches in thickness.

11. The tooth protection device as recited in claim 10, wherein the thermal layer extends intermediate the first end and the second end of said base layer.

\* \* \* \* \*